United States Patent [19]

Lemonnier

[11] Patent Number: 5,448,874
[45] Date of Patent: Sep. 12, 1995

[54] METHOD AND APPARATUS FOR REMOVING OBJECTS FROM STERILE PACKAGING

[75] Inventor: Jean Lemonnier, Vesinet, France

[73] Assignee: Millipore S.A., Saint Quentin-en-Yvelines Cedex, France

[21] Appl. No.: 107,864

[22] Filed: Aug. 17, 1993

[30] Foreign Application Priority Data

Aug. 21, 1992 [FR] France .................. 92 10193

[51] Int. Cl.6 .................................. B65B 43/26
[52] U.S. Cl. ........................ 53/381.5; 53/492
[58] Field of Search ............ 53/381.5, 492, 435, 53/382.1; 414/412

[56] References Cited

U.S. PATENT DOCUMENTS 3,419,137 12/1968 Walck, III ................ 206/364
4,586,311 5/1986 Becherer et al. ............ 53/381.5

FOREIGN PATENT DOCUMENTS 1131491 2/1957 France .

*Primary Examiner*—W. Donald Bray
*Attorney, Agent, or Firm*—Andrew T. Karnakis; Paul J. Cook

[57] ABSTRACT

The packaging is in the form of a tape comprising first and second films (4,6) between which are sandwiched objects (7) each placed in an envelope formed by a seal (8) between the films. The first method and the device (20) enable the envelopes to be opened and the objects (27) to be taken therefrom easily. The microbiological analysis method uses a tape with alternating filter membranes for the liquid to be analyzed and absorbent pads for a nutrient medium.

17 Claims, 7 Drawing Sheets

METHOD AND APPARATUS FOR REMOVING OBJECTS FROM STERILE PACKAGING

BACKGROUND

The invention is in the field of packaging devices and methods. In particular, the invention concerns a method and apparatus for opening sterile envelopes to take out an object packaged therein.

The object is, for example, a filter membrane used for microbiological analysis of liquids marketed in a sterile condition between two protective films of the same diameter, the combination being placed in an envelope. This keeps the membrane sterile until it is opened and can even be used for sterilization if at least one side is made from a paper permeable to a sterilizing gas (ethylene oxide or ETO).

SUMMARY OF THE INVENTION

The invention is directed to facilitating the task of the user who must open an envelope of the kind described above and take out the object packaged therein.

In a first aspect, a packaging in the form of a tape having a plurality of envelopes is disposed one behind the other with a predetermined pitch, said tape comprising first and second films between which are sandwiched a plurality of objects each disposed in one envelope. Each envelope is formed by sealing said first and second films around the object that it contains, each seal being able to be broken by separating the first and second films at it, said first and second films being resistant to traction all along the tape.

Unlike the prior art envelope, which is a single envelope, the packaging in accordance with the invention comprises a plurality of envelopes.

The user can open the envelopes of the tape manually one by one by taking one of the films in each hand and pulling them apart at the envelope to unseal it until the object is accessible. Moreover, the packaging in accordance with the invention is in fact designed to cooperate with mechanical means including a drive roller for each of the first and second films after the tape has passed through a separator in which the seals are broken (see below), whence the importance of the feature whereby the envelopes are disposed on the tape at a predetermined pitch and that whereby the first and second films are resistant to traction forces all along the tape (i.e. the films must not break when they are pulled to break a seal, and this includes the tape between the consecutive envelopes) will become apparent.

The packaging in accordance with the invention can facilitate the task of the user essentially because of this possibility of cooperation with such mechanical means, the operations to be effected on the latter to open an envelope being particularly easy, for example it may suffice to press the finger on a lever or on a push-button to open an envelope and offer up an object to the user in a position in which it can be grasped (see below).

According to preferred features of the packaging in accordance with the invention each seal is linear.

A relatively moderate force is then sufficient to break the seals.

According to other preferred features each seal has, in the lengthwise direction of the tape, a pointed end from which two branches diverge to a maximum separation.

The pointed end makes this an area requiring only a moderate force to separate the two films and therefore a fragile area facilitating the first stage of opening the envelope.

According to other preferred features each seal has a transverse axis of symmetry.

It is therefore possible to begin opening the envelopes from either end of the tape.

According to other preferred features each seal is hexagonal. This shape advantageously provides the above-stated seal features and is particularly suitable if the packaged object is round.

According to other preferred features the packaging comprises on each side a row of holes for cooperating with a sprocket drive.

The tape can then be driven without risk of slipping and thus compromising the operation of the mechanical means with which it is adapted to cooperate. Said rows of holes are preferably formed in the first film which is wider than the second film.

The surplus material is thus restricted to the first film as are the piercing operations required to form the lines of holes.

According to other preferred features of the packaging it comprises an integer number n of holes over a length equal to said predetermined pitch, with a marked hole each nth hole after a marked hole.

This makes it possible to position the packaging relative to the mechanical means with which it is adapted to cooperate in a particularly accurate and repetitive manner.

According to other preferred features the packaging includes a transverse fold in each gap between two consecutive envelopes so that it can be folded in accordion-fashion.

Folding is preferable to coiling because it enables objects to be kept flat and prevents them from tending to assume a curved shape after the envelope is opened.

According to other preferred features each marked hole is marked by virtue of the fact that it is provided on one of said transverse folds.

This is a particularly simple and convenient way to achieve the marking, notably because no printing operation is required.

The packaging in accordance with the invention is particularly suitable for sterile objects. In particular the first film may be made from a fluid-tight plastics material or from paper permeable to a sterilizing gas, the second film may be made from a fluid-tight plastics material and the seals are effected by welding.

Each packaged object can be a filter membrane for microbiological analysis.

In this respect, note that the package in accordance with the invention does not provide the two protective papers between which the membrane was sandwiched as in the prior art envelope because, although this goes against current perceived wisdom, it is in fact possible to dispense with such protective papers without the membrane suffering in any way.

Another sterile object for which the packaging in accordance with the invention is particularly suitable is an absorbent pad impregnated or adapted to be impregnated with a nutrient medium for carrying out microbiological analysis.

The packaging in accordance with the invention may contain only membranes or only absorbent pads but it is particularly advantageous if the packaged objects comprise a regular alternating series of m filter membrane(s) and m absorbent pad(s)) for microbiological analysis.

Packaging of this kind is particularly convenient when carrying out a microbiological analysis.

To this end, in a second aspect, the invention proposes a microbiological analysis method characterized in that:

said number m of absorbent pad(s) in m envelopes of a packaging as described above are opened;

said absorbent pad(s) is(are) impregnated with nutrient medium, if not yet impregnated, and placed in a petri dish;

m subsequent envelope(s) of said packaging is(are) opened to take out m membrane(s);

the liquid to be analyzed is filtered using said membrane(s); and each filter membrane is placed on a pad which has been placed in a petri dish and each membrane is analyzed after a growth period.

The number m will be 1, 3 or 6, for example, depending on whether a single, triple or sextuplet analysis unit is employed.

In a third aspect the invention is directed to a method for opening an envelope and removing an object packaged therein comprising the steps of a) passing the tape (1) through a separator (21) until a first envelope is in front of a first side of the separator;

b) diverging the first and second films (4,6) on a second side of the separator (21) to the first and second rollers (22,23);

c) depressing the pushbutton (36) through one rotation of roller (24), thereby breaking the seal (8) and opening the envelope by pulling at least one pitch-length (3) through the separator (21); and d) removing the object from the envelope.

At the end of each step c), the object is at the outlet of the separator with the first and second films spread apart and is therefore held in an open space from which it is particularly easy to grasp.

Furthermore, given that in each step c) the tape is advanced through the separator by a distance equal to the predetermined pitch and that the same length of the first and second films is wound onto the first and second rollers, the registration of the tape is maintained from one envelope to the next.

According to preferred features, in step b) the tape is so disposed that at the end of step c) the seal of the first envelope is not entirely broken.

Given that the operations are repetitive, the same will apply to each envelope.

Stopping at this point means that the seal of the next envelope is certain to be untouched, which is particularly important if the packaged objects are sterile.

In a first embodiment, in each step c) the first film is stretched by turning a drive roller with which the first film cooperates between the separator and the first roller, said first and second rollers being each coupled to the drive roller by a transmission arrangement such that the peripheral speed of the first and second rollers is normally slightly greater than that of the drive roller but which can slip so that the first and second rollers can be respectively braked by the first and the second films. In step b) the first film is stretched between a first edge of the separator and the drive roller and the second film is stretched between a second edge of the separator and the second roller.

With these features it is sufficient to rotate the drive roller for the tape to advance automatically in the separator and for the films to wind onto the rollers.

With the transmission arrangement provided between the drive roller and the first and second rollers all of the available length of the first and second films is sure to be wound onto the latter, in other words exactly the length of tape that has passed through the separator. It is also certain that the seal will be broken when the tape is advanced because on the second side of the separator the two films are drawn apart and each is pulled taut.

This embodiment is therefore particularly reliable, simple, convenient and economic.

In a second embodiment, in each step c) the first and second films are pulled taut directly by simultaneously rotating said first and second rollers with the same peripheral winding speed until a length equal to said predetermined pitch has been wound onto each of them.

This embodiment dispenses with the drive roller but each of the first and second rollers must be rotated and measures must be taken to ensure that the same length of the first or second film is wound onto each roller.

In a fourth aspect the invention is directed to a device suitable for implementing the method that has just been described and which comprises for cooperating with a packaging as previously explained:

a separator through which said tape can be passed to break each part of a seal which passes from a first side thereof to a second side thereof, the object being in said position in which it can be grasped from said second side when a predetermined portion of the latter has entered the separator;

first and second rollers for respectively winding said first and second films each comprising means for fixing to it a respective end of the first or second film disposed so that when an envelope is placed in front of the first side of the separator with the tape which passes through the latter and the first and second films respectively fixed to the first and second rollers the first and second films diverge between the separator and the first and second rollers;

means for driving the tape to pull on at least one of said first and second films from said second side of the separator to pull through the separator a length of the tape equal to said predetermined pitch; and means for driving said first and second rollers to rotate them by the amount which causes to be wound thereon a said length of the first and second films, respectively.

In a preferred embodiment said tape drive means comprises a drive roller for pulling on the first film with which it cooperates between the separator and the first roller. The drive means for the first and second rollers comprise between each of the latter and the drive roller a transmission arrangement such that the peripheral speed of the first and second rollers is normally slightly greater than that of the drive roller but which can slip so that the first and second rollers can be respectively braked by the first and second films, the first film being adapted to be stretched between a first edge of the separator and the drive roller and the second film between a second edge of the separator and the second roller.

In a second embodiment the drive means for the tape are formed directly by the first and second rollers and by the drive means thereof which comprise:

first and second motors for respectively rotating the first and second rollers;

first and second detector means for respectively measuring the length of the first and second films wound onto the first and second rollers;

control means connected to a triggering unit, to said first and second motors and to said first and second detector means adapted to start said motors and detector means when the triggering unit is operated to control the motors on the basis of data supplied by the detector means so that the first and second rollers have the same peripheral winding speed and to stop the motors when a length equal to said predetermined pitch has been wound onto to each roller.

The disclosure of the invention will now continue with the following description of embodiments thereof given by way of non-limiting illustrative example only with reference to the appended drawings in which:

DETAILED DESCRIPTION OF THE INVENTION

Figure 1:
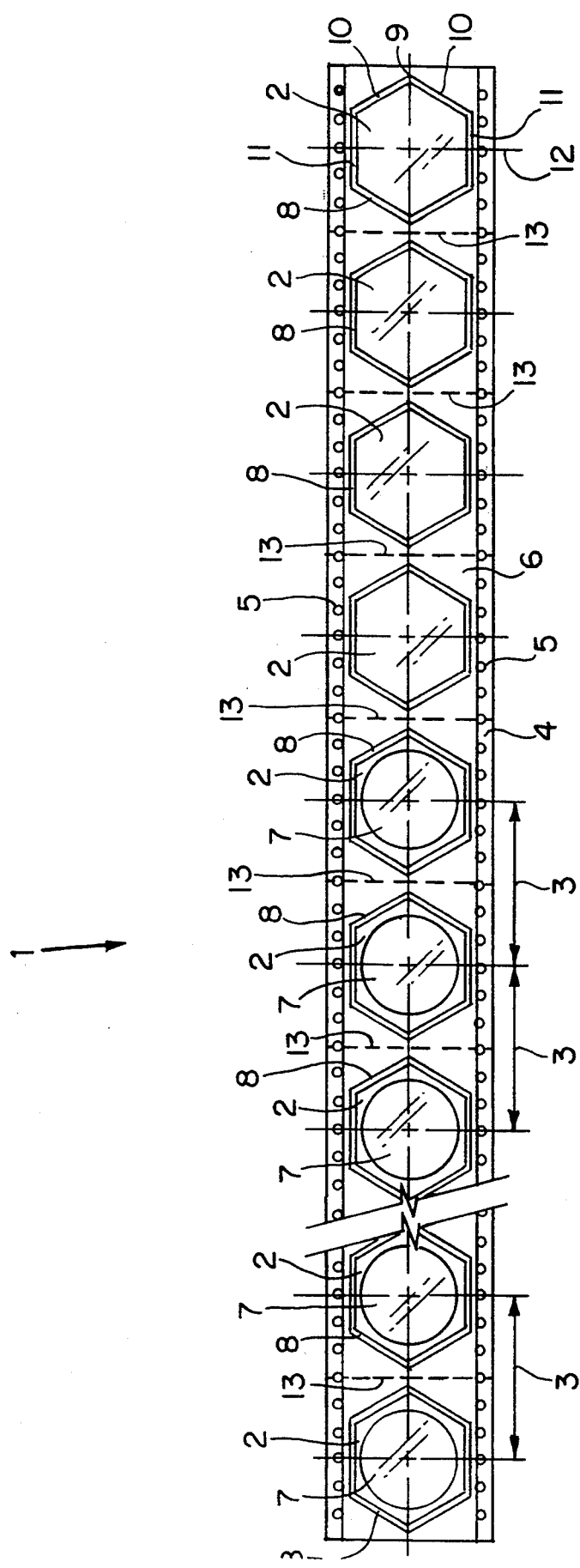
FIG. 1 shows a packaging tape in accordance with the invention flat before it is folded accordion fashion.

The tape 1 shown in FIG. 1 comprises a plurality of envelopes 2 in linear sequence with a pitch 3. The tape 1 comprises two films, a film 4 made from paper permeable to a sterilizing gas along each side of which is formed a row of holes 5 adapted to cooperate with a sprocket wheel and a film 6 made from transparent polyethylene which is narrower than the film 4. A plurality of objects 7 which are round in shape in this example are sandwiched between the films 4 and 6, each disposed in an envelope 2 formed by sealing the films 4 and 6 around the object 7 that it contains.

At the end of the tape 1 on the right-hand side in FIG. 1 there is no object 7 in the first four envelopes 2.

The films 4 and 6 are fastened together only by the seals 8 which are heat-welded and each of which can be broken by separating the two films which are resistant to traction forces all along the tape 1.

All the seals 8 are linear (approximately 3 mm wide) and are in the shape of regular hexagons with their apexes aligned so that they have one side parallel to each edge of the films 4 and 6. Looking at the seal 8 which is furthest to the right in FIG. 1, each seal 8 has, moving from right to left along the tape, a pointed end 9 from which two branches 10 diverge to a maximum separation at the two branches 11 parallel to the edges of the tape 1. As each seal 8 has a transverse axis of symmetry 12, the same would apply on movement from left to right, so that from the point of view of the operability of the envelopes 2 it does not matter which end of the tape 1 is used first.

The tape 1 is designed to be stored in a box folded in accordion-fashion, with a transverse fold 13 in each gap between two consecutive envelopes. In the example shown the folds are obtained by incising the films 4 and 6 to reduce their resistance to bending, the incisions being sized so that the films 4 and 6 retain sufficient resistance to traction forces all along the tape 1 so that they do not tear at the folds 13 when the force required to open the envelopes 2 is applied to them, especially when using the devices shown in FIGS. 2 through 9. In another embodiment the folds 13 are not incised but merely pre-marked.

Note that for each length equal to the pitch 3 the tape 1 comprises six holes 5 on each side and that on each side there is a hole on each fold 13. This means that the sixth hole after each hole on a fold 13 is on the next fold 13.

In the example shown each object 7 is a filter membrane for microbiological analysis which has been sterilized after packaging in an envelope 2 by means of a sterilizing gas which was able to enter and leave the envelope 2 through the paper 4 which is permeable to this gas.

The tape 1 is equally suitable for packaging absorbent pads which can be impregnated with nutrient medium, also for microbiological analysis, and more generally for any type of object which is sufficiently flat to enable the two films between which it is sandwiched to be sealed around it, for example medical supplies, especially for applying dressings (compresses, etc).

Alternatively the film 6 is made from PVC and is high-frequency welded to the film 4.

In another embodiment the films 4 and 6 are both made from a fluid-tight plastic material and the contents of the envelopes are sterilized by irradiating them.

This latter embodiment is particularly suitable for packaging absorbent pads already impregnated with nutrient medium, the sealed envelope preventing the pad from drying out and producing a relatively long shelf life for the medium (three weeks, for example).

The device 20 shown in FIGS. 2 through 7 is preferably used to open the envelopes of the tape 1.

This device comprises a frame (not shown) on which are mounted a separator 21, roller 22 for the film 4 and a roller 23 for the film 6, a drive roller 24 for pulling on the film 4 and a mechanism 25 for driving the rollers 22, 23 and 24.

The separator 21 has a slot 26 through which the tape 1 passes delimited by two bars fixed at each end to a side flange of the frame, namely a round bar 27 on the side of the roller 23 and an angle-iron 28 on the side of the roller 24.

The rollers 22 and 23 are each rotatably mounted on the side flanges of the frame and both are provided with a spring clip 29 for fixing one end of the film 4 or 6 to the roller.

The roller 24 is also ratably mounted on the side flanges of the frame. Its peripheral circumference is equal to the pitch 3 and at each end it has six pins 30 adapted to cooperate with the holes 5 in the tape 1. The roller 24 must be rotated through one turn (360°) to advance the film 4 or the tape 1 by a length equal to the pitch 3, which is particularly convenient. The pins 30 and the holes 5 prevent any slipping relative to the roller 24 so that the registration of the tape 1 relative to the device 20 is preserved.

Figure 2:
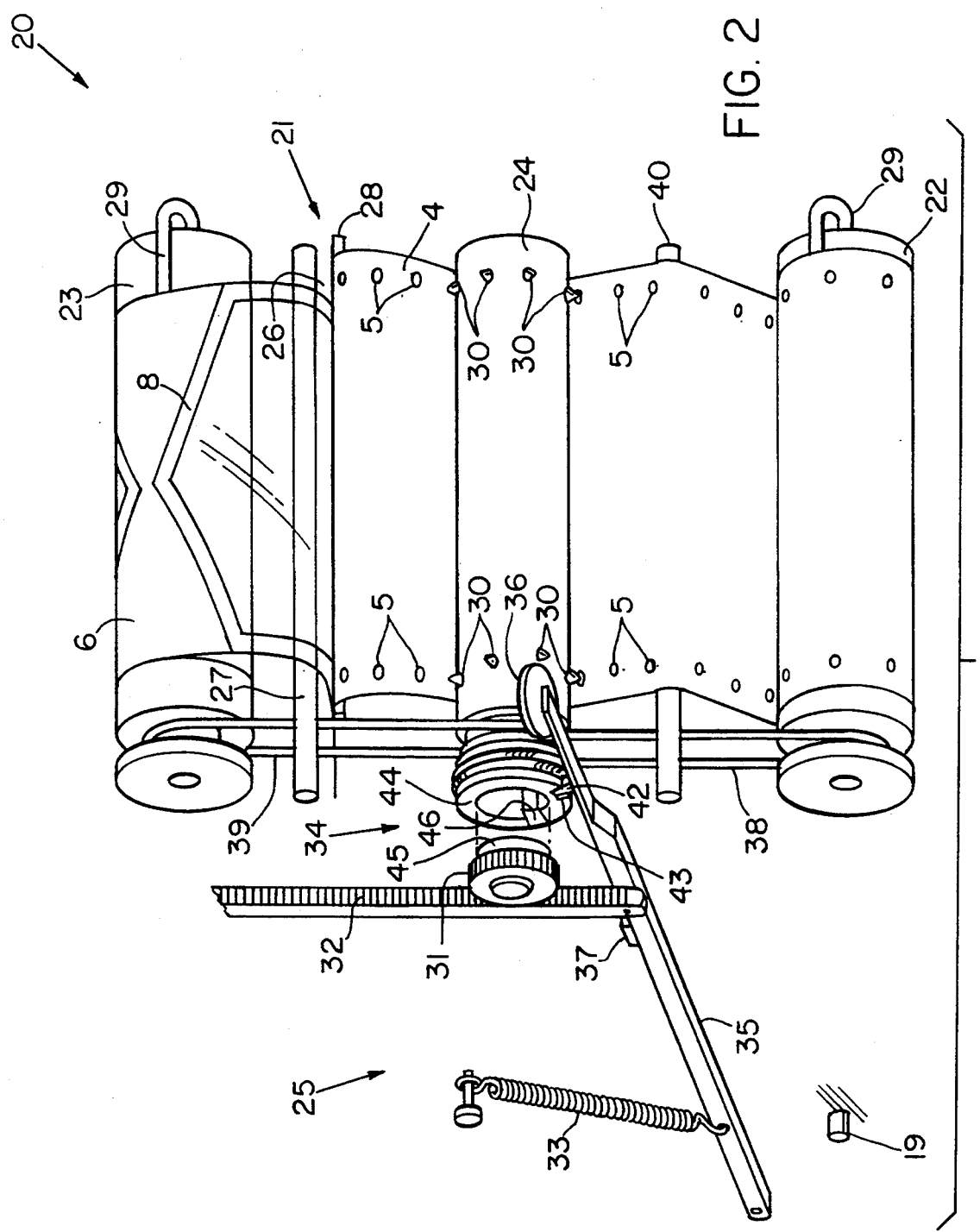
FIG. 2 is a partial view in perspective showing a device in accordance with the invention adapted to cooperate with the packaging shown in FIG. 1, FIGS. 3 through 5 show in a similar way to FIG. 2 the device in successive positions it assumes during its operation.
Figure 3:
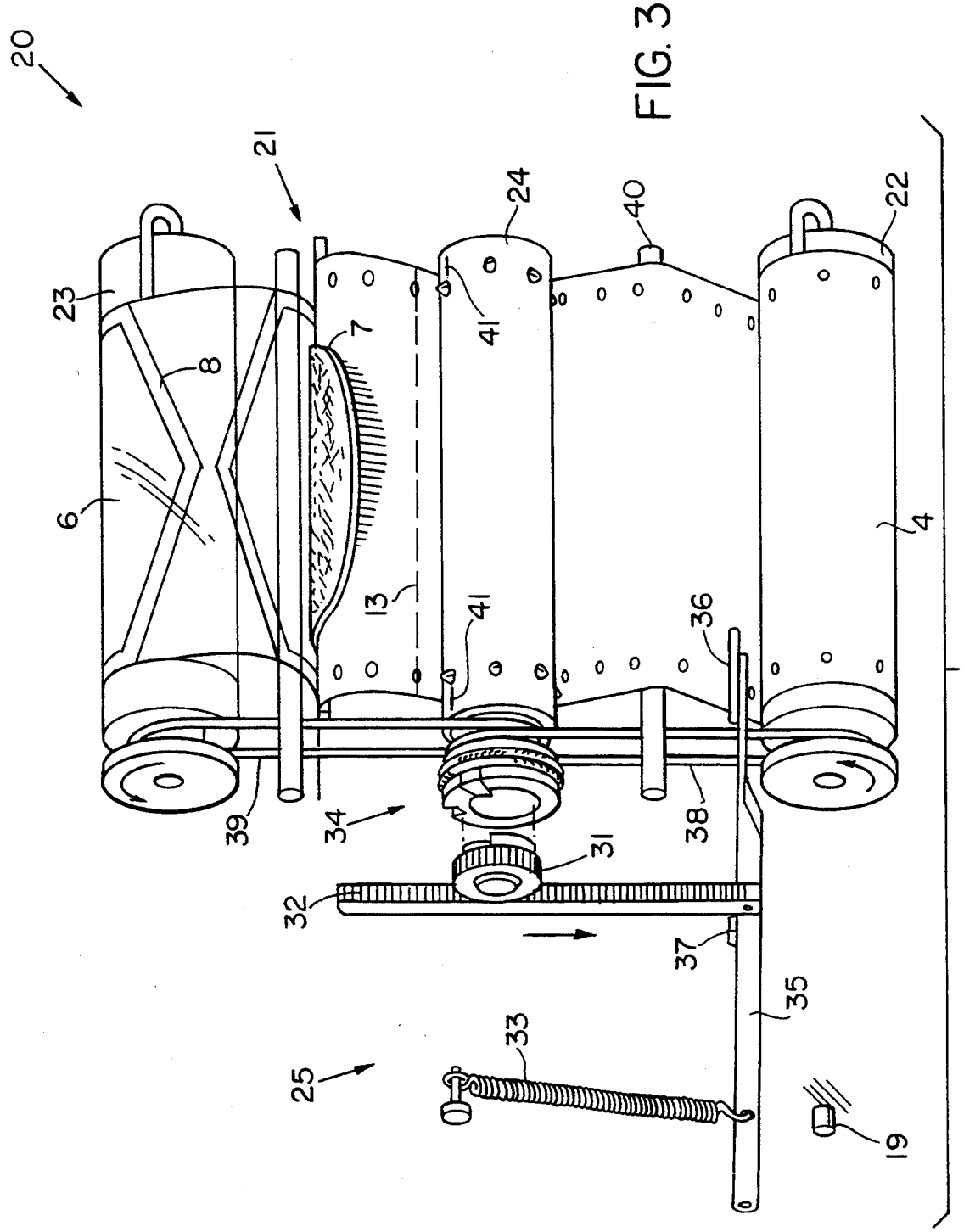
Figure 4:
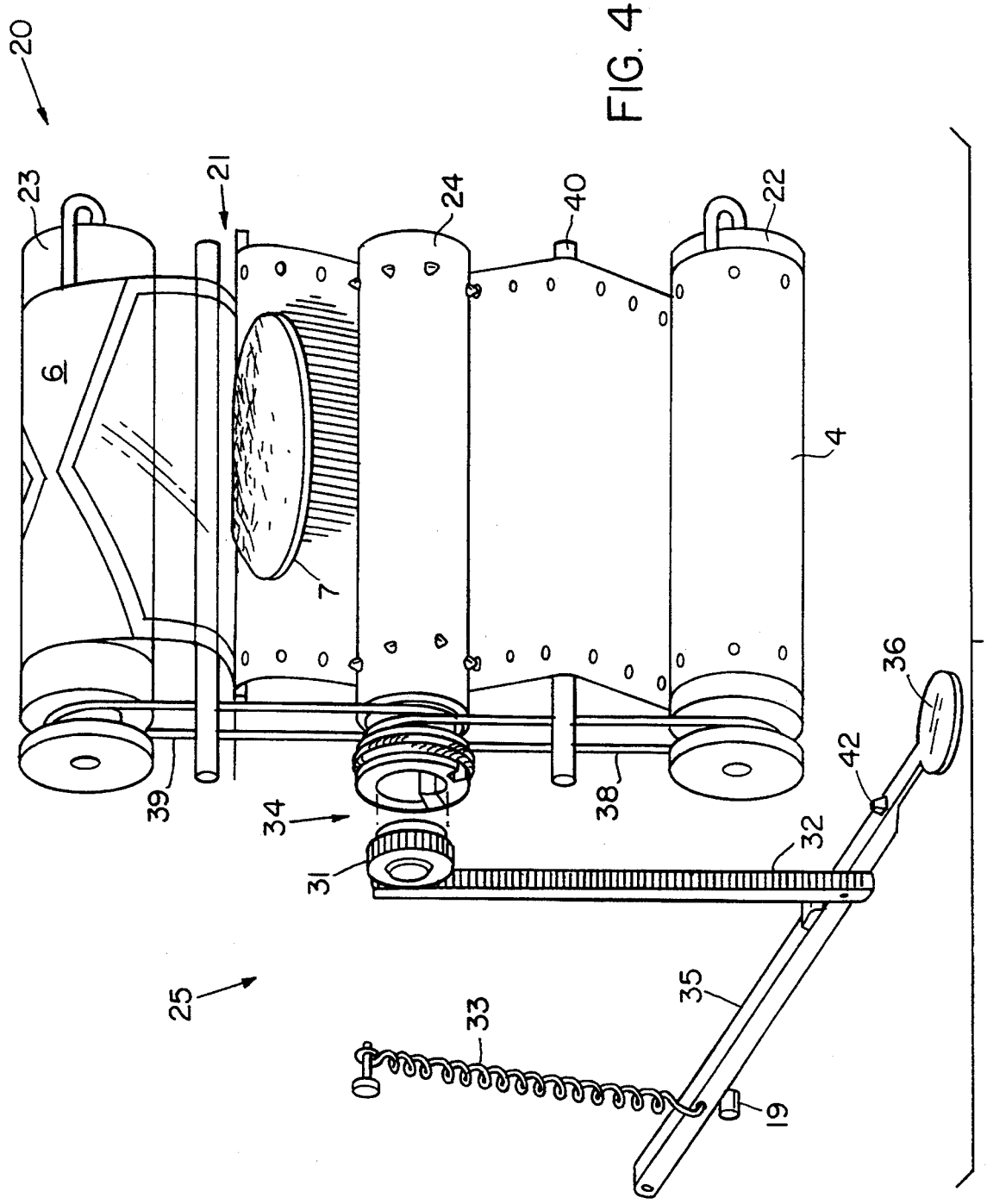
Figure 5:
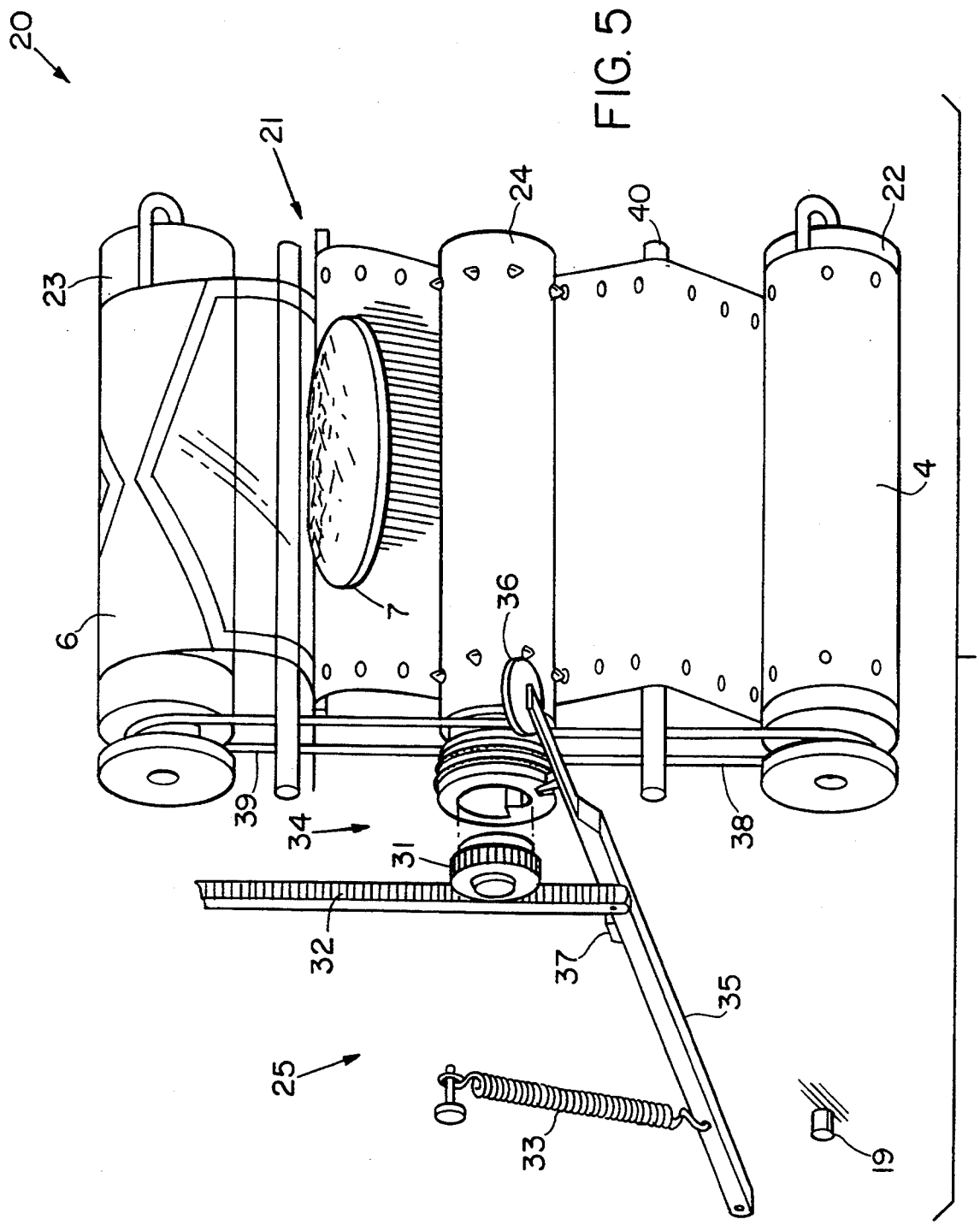

The mechanism 25 comprises a pinion 31 coaxial with and adapted to cooperate with the roller 24, a rack 32 cooperating with the pinion 31 and mobile between a first position shown in FIGS. 2 and 5 and a second position shown in FIG. 4, the pinion 31 rotating through one turn (360°) in the direction shown by an arrow in FIG. 3 when the rack passes from the FIG. 2 position to the FIG. 4 position. The pinion 31 rotates obviously one turn in the opposite direction when the rack passes from the position shown in FIG. 4 to that shown in FIG. 5. The mechanism 25 also includes spring means, in this instance the spring 33 which urges the rack 32 towards the position shown in FIGS. 2 and 5, and a coupling 34 between the pinion 31 and the roller 24 to join the two together which is shown in exploded form in FIGS. 2 through 5 for easier comprehension.

To drive the rack 32 the mechanism 25 comprises a lever 35 joined to the frame of the device at the end which is on the lefthand side in FIGS. 2 through 5. At the other end the mechanism 25 comprises a push-button 36, the rack 32 being joined at its lower end to the lever 35 with spring means (not shown) to urge it against the pinion 31, the rack 32 being in the position shown in FIGS. 2 and 5 when the lever 35 bears against an abutment (not shown) on the frame and in the position shown in FIG. 4 when it bears on the abutment 19. To absorb impacts the lever 35 bears against a rubber buffer 37 on the abutment on the frame which is not shown.

To drive the rollers 22 and 23 the mechanism 25 incorporates a transmission arrangement between each of these rollers and the roller 24 comprising a respective smooth belt 38 or 39.

The first four envelopes 2 of the tape 1 starting from the end on the right-hand side in FIG. 1 are empty because this portion of the tape is used to insert it into the device 20.

To open the fifth envelope, which is the first to contain an object 7, the tape 1 is passed through the separator 21 until this first envelope containing an object is on the side of the separator opposite the viewing side, i.e. the side of the device shown in FIGS. 2 through 5. From this viewing side one of the films 4 and 6 is taken in each hand and they are pulled apart to break the first four seals 8; the end of the film 6 is attached to the roller 23 by the spring clip 29 and the roller 23 is turned in the direction shown by an arrow in FIG. 3 until the film 6 is stretched between this roller and the edge of the separator 21 defined by the bar 27. The roller 23 is able to turn because it can slip against the smooth belt 39; the film 4 is taken backwards from the edge of the separator 21 defined by the angle-iron 28 and wound from behind onto the roller 24, taking care to stretch the film 4 between the angle-iron 28 and the roller 24. The film 4 is pulled forwards until it passes around the rod 40, the free end of the film 4 is attached to the roller 22 by the spring clip 29 and the roller 22 is turned in the direction indicated by an arrow in FIG. 3 until the film 4 is stretched between the rollers 22 and 24. The roller 22 is able to turn without turning the roller 24 because it can slip against the smooth belt 38. The situation is then that shown in FIG. 2.

To open the first envelope containing an object 7 the push-button 36 is pressed to displace the rack 32 and the pinion 31 as shown by the arrows in FIG. 3. The roller 24 turns in the same direction so that the film 4 is pulled and when the position shown in FIG. 4 is reached the roller 24 has rotated through a complete turn (360°) and the film 4 and therefore the tape 1 has advanced over a distance equal to the pitch 3. The transmission arrangement between the roller 24 and the rollers 22 and 23 causes the same length of the films 4 and 6 to be wound onto the latter rollers, the object 7 packaged in the first envelope containing any object will have then entered the separator 21 and the portion of the seal 8 that has entered the separator will have been broken.

When the push-button 36 is released the lever 35 is raised by the spring 33, the coupling 34 allows the pinion 31 to rotate freely relative to the roller 24 in the direction opposite to that shown by an arrow in FIG. 3. Consequently, in the FIG. 5 position the films 4 and 6 and the object 7 are in the same position as in FIG. 4.

Note that the object 7 is then in the middle of a free space from which the operator can readily take it.

To open the next envelope and take out the object packaged in it the user need only to repeat the same operations starting with pressing the push-button 36. Note that in the position for taking out the object (FIG. 5) the seal of the envelope that contained it has not entirely entered the separator 21 and so has not been entirely broken. The object is therefore in a position where it continues to be held by the tape 1 although it is easy to grasp and remove. Furthermore, by not breaking entirely the seal of the envelope that has just been opened, it is certain that the seal of the next envelope has not begun to be broken, which is absolutely to be avoided if the objects are sterile and must therefore not be exposed to the atmosphere other than for the minimum possible time.

To achieve the registration of the tape 1 relative to the device 20 without difficulty one of the six pins at the ends of the roller 24 is marked (see FIG. 3), in this example by a groove 41 machined near it, registration being achieved when fitting the film 4 by ensuring that a hole 5 on a fold 13 is fitted to a marked pin. In the transmission arrangement comprising the belt 39 the ratio between the diameters of the pulley carried by the roller 24 and that carried by the roller 23 is such that the peripheral speed of the roller 23 is normally slightly greater than the peripheral speed of the roller 24. However, as the belt 39 is smooth it can slip so that the roller 23 is retarded by the film 6. The tension in the belt 39 is sufficient for the film 6 to remain taut and therefore for the seals to be broken correctly when they enter the separator 21.

The above comments in respect of the belt 39 and the roller 23 are equally valid for the belt 38 and the roller 22.

The coupling 34 is such that the roller 24 rotates with the pinion 31 only when the latter rotates in the direction shown by an arrow in FIG. 3 and has reached the position relative to the roller 24 shown in FIGS. 2 through 4 and 7. The pinion 31 and the roller 24 are normally in this relative position when the rack is in the position shown in FIGS. 2 and 5 (the drawings show the device as normally adjusted).

With this adjustment the rack 32 is moved from the FIG. 2 position to the FIG. 4 position to open an envelope according to the following description. As soon as the rack 32 moves and therefore as soon as the pinion 31 moves in the direction shown in FIG. 3 the coupling 34 is engaged, and the roller 24 rotates with the pinion 31. The roller 24 has rotated through one turn when the rack reaches the position shown in FIG. 4. When the rack is released the spring 33 returns it to the position shown in FIG. 5, the pinion not moving with the roller because the latter is rotating in the direction opposite that shown in FIG. 3. When the rack returns to the FIG. 5 position the pinion 31 and the roller 24 are in the initial relative position and everything is ready for repeating the maneuver on the next envelope. If the rack 32, to be more precise the lever 35, is inadvertently released before reaching the FIG. 4 position the roller 24 will remain in the position that it reached just prior to release of the lever because the pinion 31 will no longer rotate with it when the spring returns it to the FIG. 2 or FIG. 5 position. When the rack is actuated again to move it to the position shown in FIG. 4 the pinion 31 rotates freely until the rack 32 reaches the position from which it was released, at which point the pinion commences to rotate with the roller.

The aforementioned features of the coupling 34 mean that each time the FIG. 4 position is reached the roller 24 is sure to have rotated through one turn relative to the previous time the rack reached this position. Also the pinion and the drive roller will then return automatically to the correct relative position when the rack returns to the position shown in FIGS. 2 and 5.

Note that a coupling of this kind is practical, convenient and economic and is particularly suitable when the membrane dispensing device is operated manually.

To make it easy to identify the correct relative position of the pinion 31 and the roller 24 marker means are provided in the form of a peg 42 on the lever 35 and a notch 43 on a ring 44 fastened to the roller 24. The correct relative position is when the peg 42 in the notch 43.

Note that in addition to providing this marker function the peg and the notch can also be used to lock the roller 24 and the pinion 31 in this correct relative position when the rack 32 is in the position of FIGS. 2 and 5.

Figure 6:
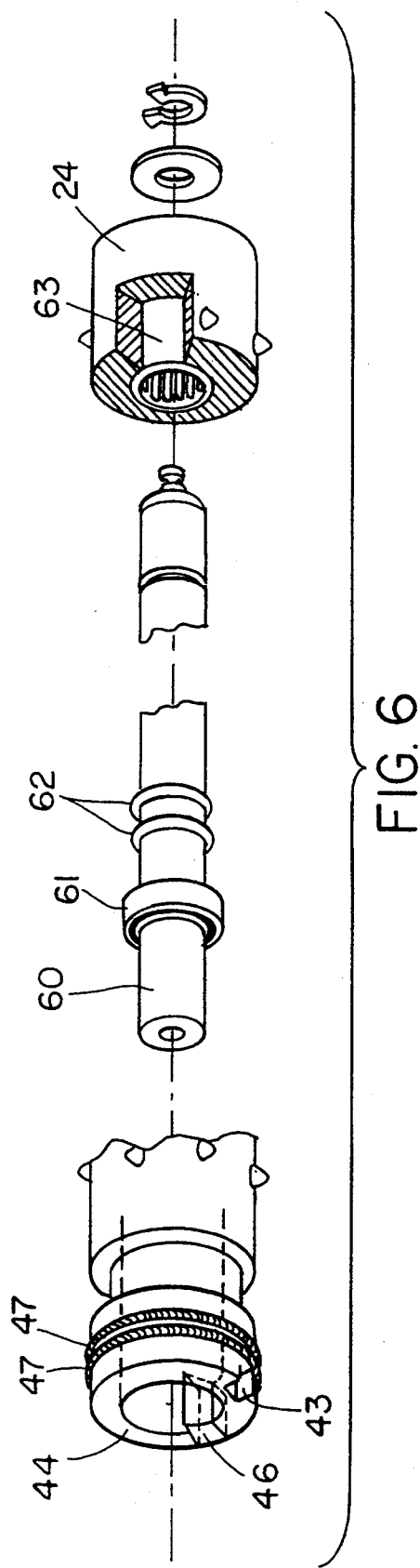
FIG. 6 is a partially cut away exploded view of a drive roller of this device.
Figure 7:
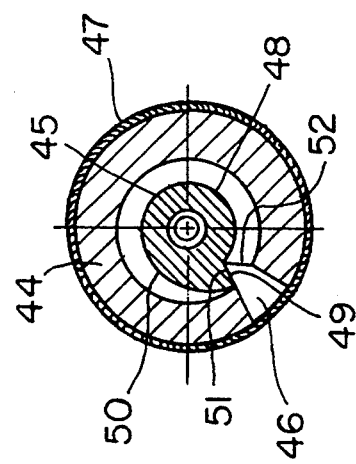
FIG. 7 is a view in elevation and transverse cross-section between the pinion and the drive roller.

In the example shown, and as seen most clearly in FIG. 6 and 7, the coupling 34 comprises a ring 44 fastened to the driver roller 24, a cam 45 fastened to the pinion 31 and disposed inside the ring 44, a key 46 sliding radially in the ring 44 and spring means in the form of two bracelet springs 47 which urge the key 46 towards the interior of the ring 44.

The cam 45 has a peripheral surface having a cylindrical portion 48, a radial portion 49 with a first end merging with a first end of the portion 48 and a curved portion 50 between a second end of the portion 48 and a second end of the portion 49.

The key 46 is normally in the position shown in which a radial surface 51 opposite a curved surface 52 projects into the ring 44. The position of the key 46 shown is an internal abutment position defined by contact between the facing surfaces of the key 46 and the ring 44 which are slightly convergent in the direction towards the interior of the ring 44.

In the predetermined relative position previously mentioned the surfaces 49 and 51 are in contact. The surface 51 is urged towards the surface 49 when the pinion 31 is urged in the direction shown in FIG. 3. When the pinion 31 is urged in the opposite direction the cam 45 rotates freely in the ring, including when its surface 50 contacts the surface 52 of the key 46, the curved surfaces 50 and 52 having a slope such that the key then retracts outwards against the springs 47 to allow the cam 45 to pass.

Note that the coupling just described is particularly suitable for the device 20 but can be used in other devices.

Referring to FIG. 6, the roller 24 is journalled about a central shaft 60 fixed to the frame of the device with one or more ball bearings 61, one or more O-rings 62 and a one-way coupling 63 between the shaft 60 and the roller 24.

The non-return one-way coupling 63 prevents the roller 24 from rotating in the direction opposite that shown in FIG. 3 to prevent the films 4 and 6 from loosening and the device 20 losing its adjustment.

The O-rings 62 prevent the roller 24 from continuing to rotate due to its inertia when the rack 32 reaches the end of its travel (FIG. 4) which would also cause the device 20 to lose its adjustment.

Note that winding the film 4 onto the roller 24 from behind by taking it backwards on the input side of the roller while it is taken forwards on the output side maximizes the length of contact between the film 4 and the roller 24 and consequently, in the example shown, maximizes the number of pins 30 in engaging the holes 5. This limits the risk of the holes in the film 4 tearing when the latter is pulled.

Figure 8:
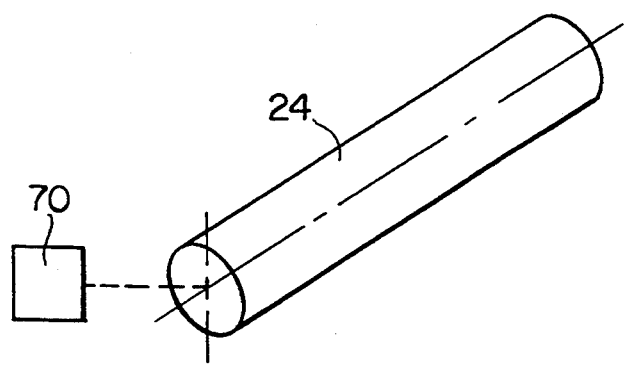
FIGS. 8 and 9 show alternative embodiments.

In the embodiment shown in FIG. 8 the device for opening the envelopes is simpler, the roller 24 being driven no longer by mechanical means (including the coupling 34, pinion 31, rack 32 and lever 35) but by a motor 70 which is caused to rotate by exactly one turn each time it is energized. A stepper motor, for example, can be used.

Note that depending on individual circumstances the tape 1 may be advanced by one pitch 3 through more or less than one turn of the roller 24, in which case the mechanism 25 or the motor 70 is adapted accordingly.

Figure 9:
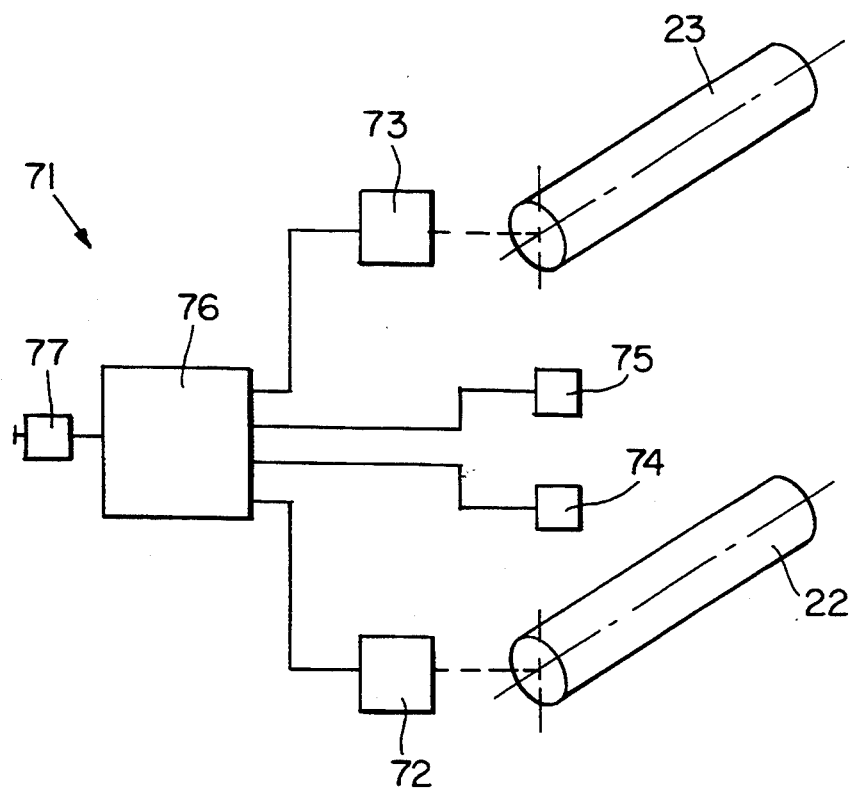

In the embodiment shown in FIG. 9 there is no driver roller 24 or mechanism 25. To open an envelope the films 4 and 6 are pulled directly by turning the rollers 22 and 23 together at the same peripheral winding speed until each has wound on a length equal to the pitch 3.

The drive means 71 for the driver rollers 22 and 23 comprise a motor 72 for driving the roller 22 and a motor 73 for driving the roller 23, detector or sensor means 74 for measuring the length of film 4 wound onto the roller 22, sensor means 75 for measuring the length of film 6 wound onto the roller 23 and a control unit 76 connected to the motors 72 and 73, to the detector means 74 and 75 and to a push-button or operating member 77.

When the member 77 is operated the unit 76 starts the motors 72 and 73 and controls them on the basis of information supplied by the sensors 74 and 75 so that the rollers 22 and 23 turn at the same peripheral winding speed, the unit 76 stopping the motors when each has wound on a length equal to the pitch 3.

Numerous variants of the device 20 are feasible; for example, a different separator may be provided having on its entry side a brake for the tape 1, the seals 8 being broken when the film 4 passes over an edge of the kind provided by the angle-iron 28, in which case the film 6 does not need to be stretched.

With regard to the tape 1, the above description assumes starting from the end on the right in FIG. 1 by leaving four envelopes empty to economize on the objects. However depending on individual circumstances it may be more economical to provide objects anyway in the first few envelopes or to dispense with seals in the end part of the tape.

A starting section may also be provided on both sides of the tape, rather than on one side only as in FIG. 1.

More generally, the invention is not limited to the examples described and shown.

What is claimed is:

1. For use with a sealed package having an object placed therein, said package being incorporated as part of a continuous tape having a predetermined pitch and including a plurality of sealed packages, each of said sealed packages being formed by sealing film layers along a seal region so as to encapsulate said object, said film layers being resistant to breaking when pulled along the length of said tape, an improved apparatus for opening said sealed package comprising:

separator means adapted to receive the leading edge of said tape and to permit said tape to pass from a first side to a second side thereof for breaking the seal at a portion of said seal region whereby said film layers are split apart to form respective first and second film layers;

first and second rotatable rollers for respectively receiving the ends of said first and second film layers to permit said layers to be wound thereon;

means for fixing to said rollers the ends of said film layers;

means for driving said tape to pull from said second side on at least one of said first and second film layers to pull through said separator means a length of said tape equal to said predetermined pitch;

said rollers being positioned with respect to said separator means such that with the ends of said first and second film layers respectively affixed to said first and second rollers the film layers of said sealed package will diverge in the region between said separator means and said first and second rollers; and means for driving said first and second rollers to rotate said rollers by an amount which causes to be wound thereon a length of said tape equal to said predetermined pitch.

2. The apparatus according to claim 1 wherein said tape drive means comprises:

a rotating drive roller for pulling on said first film layer affixed to said first roller;

transmission means for maintaining the peripheral speed of said first and second rollers slightly greater than that of said drive roller while allowing slippage between said first and second rollers and said drive roller such that said first and second rollers can be stopped respectively by said first and second film layers, said first film layer being adapted to be stretched between a first edge of said separator means and said drive roller and said second film layer between a second edge of said separator means and said second roller.

3. The apparatus according to claim 2 wherein said drive roller has a peripheral circumference equal to said predetermined pitch so that said drive roller must be rotated by one turn to open one of said sealed packages.

4. The apparatus according to claim 3 including peripheral means for rotating said drive roller, said peripheral means comprising:

a pinion coaxial with said drive roller;

a rack cooperating with said pinion and movable between a first position and a second position, said pinion rotating by one turn in one direction when the rack passes from said first to said second position and by one turn in the opposite direction when said rack moves from said second to said first position;

spring means for urging said rack towards said first position; and coupling means between said pinion and said drive roller such that said drive roller rotates with said pinion only when said pinion rotates in the first direction and has reached a predetermined position relative to said drive roller, said pinion and said drive roller being normally in said predetermined relative position when said rack is in said first position.

5. The apparatus according to claim 4 including means for marking said predetermined relative position when said rack is in said first position.

6. The apparatus according to claim 4 further including a lever joined to said rack at a first end and having a push-button at a second end, said rack being joined at one end to said lever with spring means for urging it against said pinion, said rack being in said first and second positions when said lever bears respectively against first and second abutments.

7. The apparatus according to claim 6 wherein said lever comprises a peg which engages a notch in said drive roller when said rack is in said first position and said pinion and said drive roller are in said predetermined relative position.

8. The apparatus according to claim 4 wherein said coupling means between said pinion and the said drive roller comprises:

a ring fastened to said drive roller;

a cam fastened to said pinion and disposed inside said ring having a peripheral surface comprising a cylindrical portion, a radial portion a first end of which merges with a first end of said cylindrical portion, and a curved portion between a second end of said cylindrical portion and a second end of the radial portion;

a key adapted to slide in a radial direction in said ring, said key having an inner position in which a radial surface opposite a curved surface projects into said ring;

spring means for urging said key towards said inner position;

whereby said radial surfaces of said key and of said cam being in contact when said pinion and said drive roller are in said predetermined relative position, the radial surface of said cam being urged towards the radial surface of said key when said pinion is urged in said first direction; whereas when the pinion is urged in the second direction said cam rotates freely in said ring including when the curved surface of said cam contacts the curved surface of said key, said curved surfaces having a slope such that said key is then retracted outwards to allow said cam to pass.

9. The apparatus according to claim 2 wherein means for rotating said drive roller comprises an electric motor adapted to rotate by a predetermined amount each time that it is energized.

10. The apparatus according to claim 2 wherein said drive roller comprises at each end pins adapted to cooperate with holes formed along the edges of said first film layer.

11. The apparatus according to claim 10 wherein said drive roller comprises means for marking one of said pins.

12. The apparatus according to claim 2 including a non-return coupling to allow said drive roller to rotate only in said first direction.

13. The apparatus according to claim 2 including at least one O-ring to brake said drive roller so that it does not continue to rotate due to its inertia when said roller ceases to be driven.

14. The apparatus according to claim 2 wherein said transmission means between said drive roller and said first and second rollers comprises a smooth belt.

15. The apparatus according to claim 1 wherein said tape drive means comprises:
first and second motors for respectively rotating the first and second rollers;
first and second detector means for respectively measuring the length of said first and second film layers wound onto said first and second rollers;
control means connected to a trigger unit, to said first and second motors and to said first and second detector means adapted to start said motors and detector means when said trigger unit is activated to control said motors on the basis of data supplied by said detector means so that said first and second rollers have the same peripheral winding speed, and adapted to stop said motors when a length of tape equal to said predetermined pitch has been wound onto each of said rollers.

16. The apparatus according to claim 1 wherein each of said first and second rollers includes a spring clip for fixing thereto said first and second film layers respectively.

17. The apparatus according to claim 1 wherein said separator means includes a slot through which said tape is passed.

* * * * *